United States Patent
Nabatame (10) Patent No.: US 8,989,341 B2
(45) Date of Patent: Mar. 24, 2015

(54) X-RAY CT APPARATUS

(71) Applicant: Takeo Nabatame, Otaware (JP)

(72) Inventor: Takeo Nabatame, Otaware (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 185 days.

(21) Appl. No.: 13/687,504

(22) Filed: Nov. 28, 2012

(65) Prior Publication Data

US 2013/0089176 A1    Apr. 11, 2013

Related U.S. Application Data

(63) Continuation of application No. PCT/JP2011/075468, filed on Nov. 4, 2011.

(30) Foreign Application Priority Data

Nov. 5, 2010    (JP) ................................ 2010-249029

(51) Int. Cl.
*A61B 6/00* (2006.01)
*G01N 23/04* (2006.01)
*A61B 6/03* (2006.01)

(52) U.S. Cl.
CPC .............. *G01N 23/046* (2013.01); *A61B 6/032* (2013.01); *A61B 6/461* (2013.01); *A61B 6/544* (2013.01); *G01N 2223/419* (2013.01); *G01N 2223/612* (2013.01)
USPC .................................................. 378/8; 378/4

(58) Field of Classification Search
USPC ......................................................... 378/8, 4
See application file for complete search history.

(56) References Cited

U.S. PATENT DOCUMENTS 5,148,460 A       9/1992   Aichinger
2008/0240336 A1*  10/2008  Miyazaki et al. ................. 378/4

FOREIGN PATENT DOCUMENTS

| JP | 7-204196 A    | 8/1995  |
| JP | 11-299765 A   | 11/1999 |
| JP | 2000-152924 A | 6/2000  |
| JP | 2004-089430 A | 3/2004  |
| JP | 2004-135860 A | 5/2004  |

(Continued)

OTHER PUBLICATIONS

International Preliminary Report on Patentability issued May 8, 2013 in PCT/JP2011/075468 filed Nov. 4, 2011 submitting English translation only.

Written Opinion issued Feb. 14, 2012 in PCT/JP2011/075468 filed Nov. 4, 2011 submitting English translation only.

(Continued)

*Primary Examiner* — Hoon Song
(74) *Attorney, Agent, or Firm* — Oblon, McClelland, Maier & Neustadt, L.L.P.

(57) ABSTRACT

According to one embodiment, an X-ray CT apparatus includes a body thickness information acquiring unit, a threshold determining unit and an image generating unit. The body thickness information acquiring unit acquires information of a body thickness of an object. The threshold determining unit determines a threshold of an exposure dose according to the body thickness of the object. The image generating unit generates an image indicating a relationship between the body thickness of the object and the threshold and displays a generated image on a display unit.

9 Claims, 6 Drawing Sheets

(56) References Cited

FOREIGN PATENT DOCUMENTS

| | | |
|---|---|---|
| JP | 2005-143759 A | 6/2005 |
| JP | 2005-270286 A | 10/2005 |
| JP | 2005-296277 A | 10/2005 |
| JP | 2009-050361 A | 3/2009 |
| JP | 2009-213709 A | 9/2009 |

OTHER PUBLICATIONS

International Search Report mailed on Feb. 14, 2102, issued for International Application No. PCT/JP2011/075468, filed Nov. 4, 2011 (with English Translation of the Categories).
Chinese Office Action issued Jan. 4, 2015, in Patent Application No. 201180003587.6.

* cited by examiner

FIG. 1

| BODY THICKNESS t/mm | CLASSIFICATION | SET THRESHOLD Th | |
|---|---|---|---|
| | | ADULTS | CHILDREN |
| 500>t≧400 | LL | Th_A | Th_a |
| 400>t≧320 | L | Th_B | Th_b |
| 320>t≧240 | M | Th_C | Th_c |
| 240>t≧180 | S | Th_D | Th_d |
| 180>t | SS | Th_E | Th_e |

X-RAY CT APPARATUS

CROSS-REFERENCE TO RELATED APPLICATIONS

This application is a Continuation Application of No. PCT/JP2011/075468, filed on Nov. 4, 2011, and the PCT application is based upon and claims the benefit of priority from Japanese Patent Application No. 2010-249029, filed on Nov. 5, 2010, the entire contents of which are incorporated herein by reference.

FIELD

Embodiments described herein relate generally to an X-ray CT (Computed Tomography) apparatus.

BACKGROUND

It is desirable that an operator of an X-ray CT apparatus control an exposure dose received by an object so as not to apply excess X-rays to the object. Thus, in order to control exposure doses received by objects, for example, a conventional technique has been proposed that total DLP (Dose Length Product) and maximum or average CTDIvol (volume CT Dose Index) are displayed for operators based on scan conditions.

A threshold level of X-ray exposure doses received by objects varies depending upon ages, sites to be photographed, and body types of the objects. However, conventional techniques control the exposure dose using a sum exposure dose from an overall scan. Thus, it is difficult for the conventional techniques to control the exposure dose depending upon a scan area of an object.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinbelow, a description will be given of an X-ray CT apparatus according to embodiments of the present invention with reference to the drawings.

In general, according to one embodiment, an X-ray CT apparatus includes a body thickness information acquiring unit, a threshold determining unit and an image generating unit. The body thickness information acquiring unit acquires information of a body thickness of an object. The threshold determining unit determines a threshold of an exposure dose according to the body thickness of the object. The image generating unit generates an image indicating a relationship between the body thickness of the object and the threshold and displays a generated image on a display unit.

Figure 1:
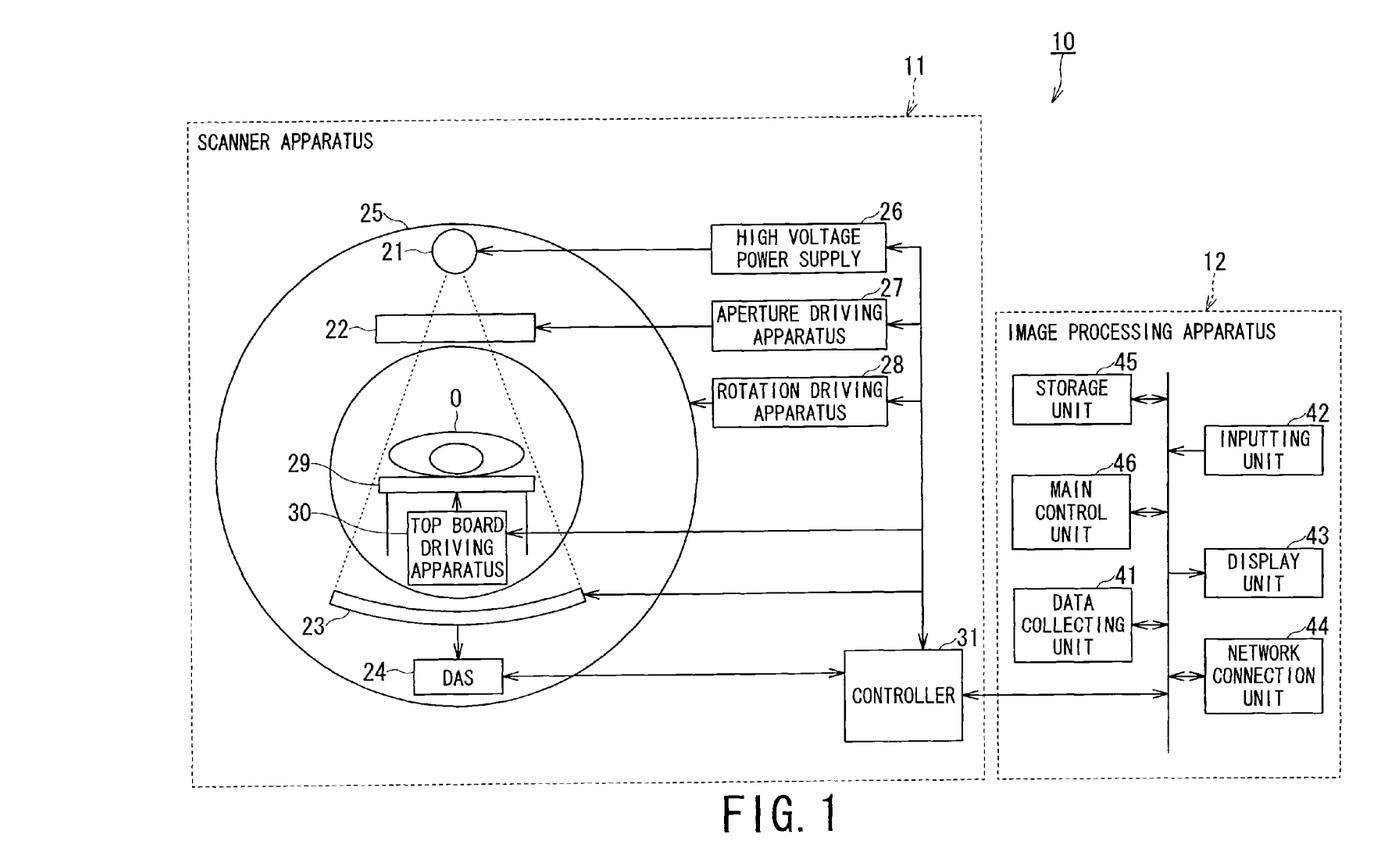
FIG. 1 is a schematic block diagram illustrating an entire configuration of an exemplary X-ray CT apparatus according to an embodiment of the present invention.

FIG. 1 is a schematic block diagram illustrating an entire configuration of an exemplary X-ray CT apparatus 10 according to an embodiment of the present invention.

The X-ray CT apparatus 10 includes a scanner apparatus 11 and an image processing apparatus 12. The scanner apparatus 11 of the X-ray CT apparatus 10 is usually installed in an examination room. The scanner apparatus 11 generates X-ray transmission data about a site of a patient O (object). The image processing apparatus 12 is usually installed in a control room adjacent to the examination room. The image processing apparatus 12 generates projection data based on the transmission data to generate and display a reconstruction image.

The scanner apparatus 11 of the X-ray CT apparatus 10 includes an X-ray tube 21, an aperture 22, an X-ray detector 23, a DAS (Data Acquisition System) 24, a rotation unit 25, a high voltage power supply 26, an aperture driving apparatus 27, a rotation driving apparatus 28, a couch top 29, a couch top driving apparatus 30, and a controller 31.

The high voltage power supply 26 applies voltage (hereinafter, referred to as the tube voltage) to the X-ray tube 21, and thereby the X-ray tube 21 generates X-rays. The X-rays generated by the X-ray tube 21 are applied to the patient O as fan beam X-rays or cone beam X-rays.

The aperture 22 is controlled by the controller 31 through the aperture driving apparatus 27 and adjusts an area being irradiated by the X-ray tube 21 with the X-rays in a slice direction.

The X-ray detector 23 is composed of one or more X-ray detecting elements (electrical charge accumulating elements). The X-ray detecting elements sense X-rays applied from the X-ray tube 21. The X-ray tube 21 and the X-ray detector 23 face each other across the patient O placed on the couch top 29 and are supported by the rotation unit 25.

As the X-ray detector 23, a one-dimensional array type (single-slice type) detector having a plurality of channels arranged in a channel (CH) direction and a single row of X-ray detecting elements arranged in the slice direction can be used, for example. Also, a two-dimensional array type (multi-slice type) detector having a plurality of channels arranged in the channel (CH) direction and multiple rows of X-ray detecting elements arranged in the slice direction may be used.

The DAS 24 amplifies signals of the transmission data sensed by the X-ray detecting elements constituting the X-ray detector 23, converts the signals into digital ones, and outputs the digital signals. Output data of the DAS 24 is sent to the image processing apparatus 12 through the controller 31 of the scanner apparatus 11.

The rotation unit 25 holds therein the X-ray tube 21, the aperture 22, the X-ray detector 23, and the DAS 24 simultaneously. When the rotation driving apparatus 28 causes the rotation unit 25 to rotate under the control of the controller 31, the X-ray tube 21, the aperture 22, the X-ray detector 23, and the DAS 24 also simultaneously rotate around the patient O.

The high voltage power supply 26 supplies the X-ray tube 21 with power required to apply X-rays, under the control of the controller 31.

The aperture driving apparatus 27 adjusts an opening of the aperture 22 to modify an X-ray irradiation area in the slice direction, under the control of the controller 31.

The rotation driving apparatus 28 rotates the rotation unit 25 around a cavity portion, under the control of the controller 31.

The couch top 29 is configured so that the patient O can be placed thereon.

The couch top driving apparatus 30 moves the couch top 29 up and down, under the control of the controller 31. Also, the couch top driving apparatus 30 moves the couch top 29 to an X-ray irradiation field of an opening portion at the center of the rotation unit 25, under the control of the controller 31.

The controller 31 includes a CPU, storage mediums such as RAM and ROM, and the like. The controller 31 performs a scan by controlling the X-ray detector 23, the DAS 24, the high voltage power supply 26, the aperture driving apparatus 27, the rotation driving apparatus 28, and the couch top driving apparatus 30 in accordance with programs stored in the storage mediums. The RAM of the controller 31 provides a work area in which programs executed by the CPU and data are temporarily stored. The storage mediums such as the ROM of the controller 31 store a startup and a control program for the scanner apparatus 11 as well as various types of data needed to execute these programs.

It should be noted that the storage mediums such as the ROM of the controller 31 may include a magnetic or an optical recording medium or a CPU-readable recording medium such as semiconductor memory, and some or all of the programs and data in the storage mediums may be downloaded via an electronic network.

On the other hand, the image processing apparatus 12 of the X-ray CT apparatus 10 is a personal computer, for example and can transmit and receive data to and from a network such as a backbone LAN (Local Area Network) in a hospital.

As illustrated in FIG. 1, the image processing apparatus 12 includes a data collecting unit 41, an inputting unit 42, a display unit 43, a network connection unit 44, a storage unit 45, and a main control unit 46.

The data collecting unit 41 collects projection data obtained by the scan performed by the scanner apparatus 11 via the DAS 24 and the controller 31. The data collected by the data collecting unit 41 is stored in the storage unit 45.

The inputting unit 42 is a common inputting device such as a keyboard, a touch panel, and a numeric keypad. The inputting unit 42 outputs operation input signals corresponding to user's operations to the main control unit 46.

The display unit 43 is a common display apparatus such as a liquid crystal display and an OLED (Organic Light Emitting Diode) display. The display unit 43 displays a variety of images such as a scanogram, under the control of the main control unit 46.

In the network connection unit 44, a variety of information communications protocols according to network types are implemented. The network connection unit 44 connects the image processing apparatus 12 to other electrical equipment in accordance with the various protocols. This connection may be electrical one via an electronic network. Note that the electronic network refers to the entire information and communication networks that use telecommunications technologies, and includes a wireless/wired LAN such as a backbone LAN in a hospital and the internet as well as a telephone communication network, a fiber optic communication network, a cable communication network, and a satellite communication network.

The storage unit 45 includes a magnetic or an optical recording medium or a recording medium readable by a CPU in the main control unit 46, such as semiconductor memory. The storage unit 45 stores the data collected by the data collecting unit 41. The present embodiment describes an exemplary case in which the storage unit 45 includes at least a threshold storage unit 47 and a dose history storage unit 48.

Figure 2:
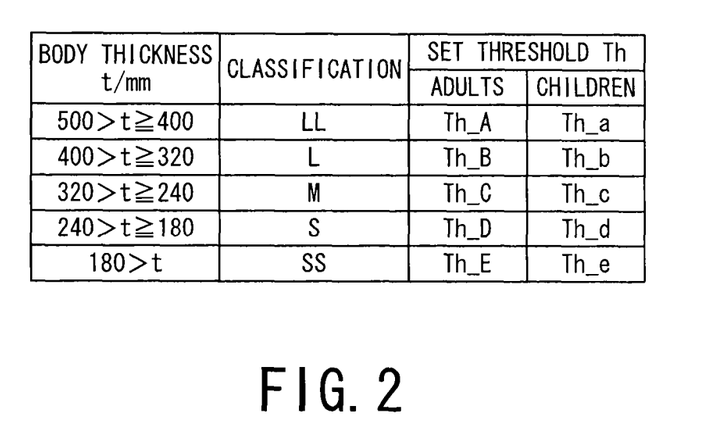
FIG. 2 is a table showing an exemplary relationship between body thicknesses and thresholds of exposure doses stored in the threshold storage unit.

FIG. 2 is a table showing an exemplary relationship between body thicknesses and thresholds of exposure doses stored in the threshold storage unit 47.

In the threshold storage unit 47, the body thicknesses and the thresholds of the exposure doses are previously associated with each other, and stored. FIG. 2 shows an exemplary case in which a threshold of an exposure dose Th based on a body thickness and an age of a patient O is previously stored in the threshold storage unit 47.

When a scan is performed, the dose history storage unit 48 stores the relationship between a radiation dose and an area on the couch top (bed) 29 in the performed scan.

The main control unit 46 includes the CPU, storage mediums such as RAM and ROM, and the like. The main control unit 46 controls the controller 31 of the scanner apparatus 11 in accordance with programs stored in the storage mediums. The RAM of the main control unit 46 provides a work area in which programs executed by the CPU and data are temporarily stored. The storage mediums such as the ROM of the main control unit 46 store a startup program for the image processing apparatus 12 and a control program for the controller 31, as well as various types of data needed to execute these programs.

It should be noted that the storage mediums such as the ROM of the main control unit 46 may include a magnetic or an optical recording medium or a CPU-readable recording medium such as semiconductor memory, and some or all of the programs and data in the storage mediums may be downloaded via an electronic network.

Figure 3:
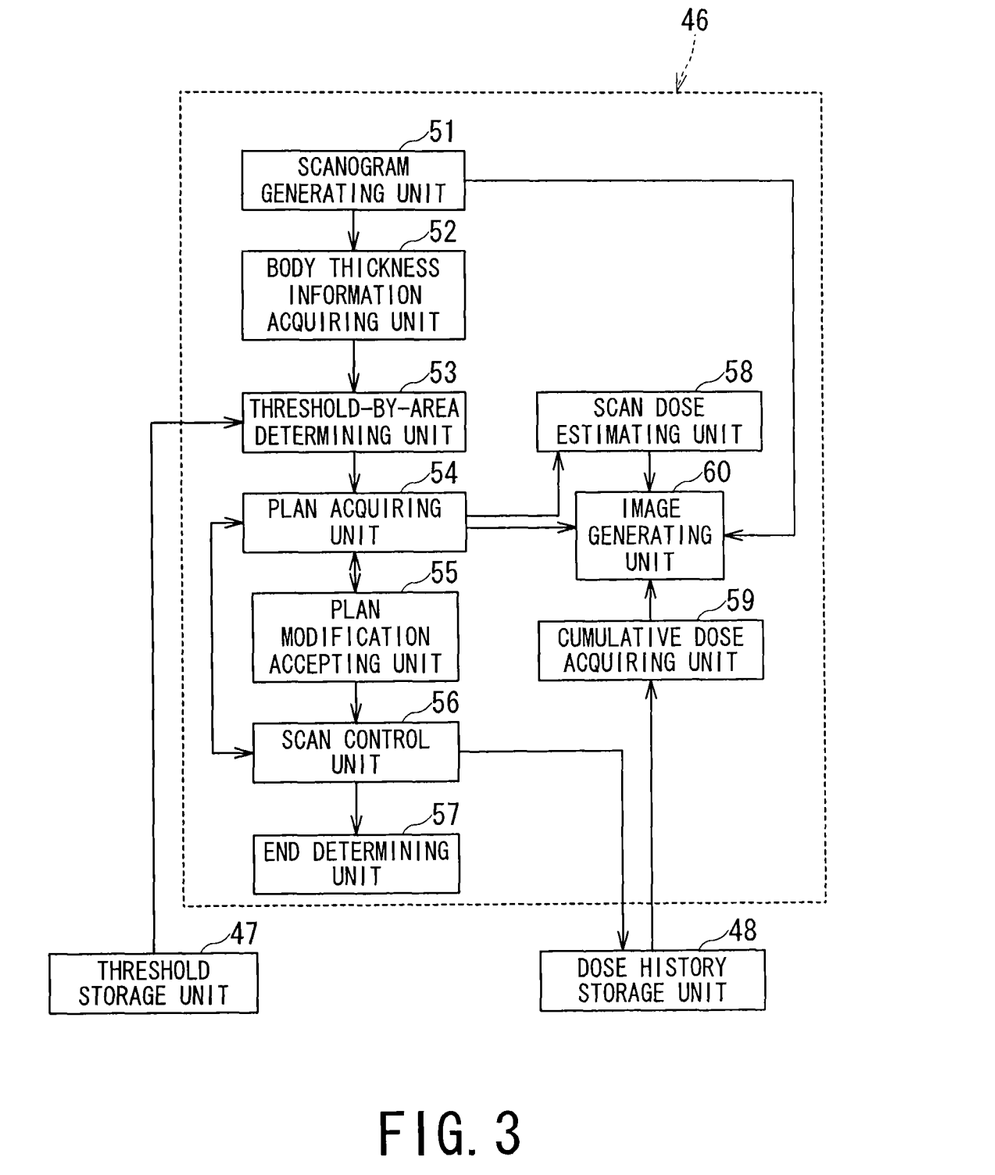
FIG. 3 is a schematic block diagram illustrating an exemplary configuration of a portion for performing functions by the CPU of the main control unit.

FIG. 3 is a schematic block diagram illustrating an exemplary configuration of a portion for performing functions by the CPU of the main control unit 46. The function performing portion may also be composed of hardware logic such as a circuit without a CPU.

As illustrated in FIG. 3, the CPU of the main control unit 46 functions, according to the programs stored in the storage mediums such as the ROM, as at least a scanogram generating unit 51, a body thickness information acquiring unit 52, a threshold-by-area determining unit (threshold determining unit) 53, a plan acquiring unit 54, a plan modification accepting unit 55, a scan control unit 56, an end determining unit 57, a scan dose estimating unit 58, a cumulative dose acquiring unit 59, and an image generating unit 60. The units 51 to 60 use the required work area of the RAM as a temporary storage area for data.

The X-ray CT apparatus 10 according to the present embodiment displays a threshold of an exposure dose according to an area of a patient O. For example, if the X-ray CT apparatus 10 obtains information of thresholds of exposure doses based on body thicknesses of the patient O and information indicating a relationship between areas on the patient O and the body thicknesses of the patient O, the X-ray CT apparatus 10 can display the threshold of the exposure dose according to the area of the patient O. The areas on the patient O can be defined as areas on the couch top 29, for example. In addition, the areas on the patient O may also be defined as pixel positions (pixel coordinates) of a picked-up image of the patient O. In the following description, the areas on the couch top 29 will be used as the areas on the patient O.

The scanogram generating unit 51 controls the controller 31 and moves the couch top 29 in a body axis direction of the patient O with the positions of the X-ray tube 21 and the X-ray detector 23 fixed. Then, the scanogram generating unit 51 generates a scanogram based on transmission data of X-rays emitted in synchronization with the movement.

The body thickness information acquiring unit 52 acquires a relationship between an area of the patient O on the couch top 29 and a body thickness of the patient O based on the scanogram data.

The threshold-by-area determining unit (threshold determining unit) 53 searches the threshold storage unit 47 based on the information of the body thickness of the patient O acquired by the body thickness information acquiring unit 52 to obtain the information of an exposure dose threshold Th associated with the body thickness (see FIG. 2). Then, the threshold-by-area determining unit 53 determines a relationship between the area on the couch top 29 and the threshold Th according to the body thickness of the patient O. Further, the threshold-by-area determining unit 53 may also calculate the threshold of the exposure dose based on the body thickness. In this case, the X-ray CT apparatus 10 may not include the threshold storage unit 47.

Figure 4:
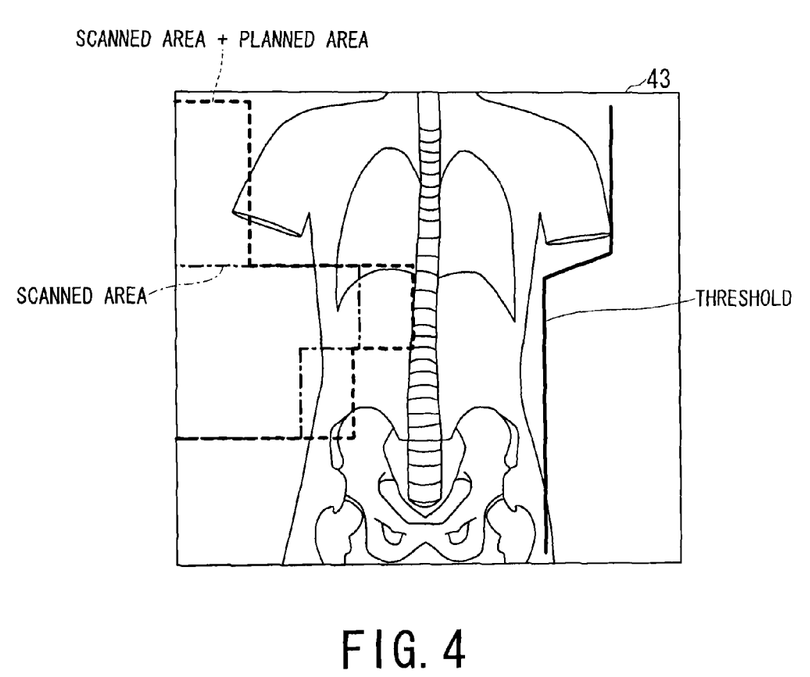
FIG. 4 illustrates an exemplary image obtained by superimposing a threshold of an exposure dose on a scanogram according to an area of a patient.

FIG. 4 illustrates an exemplary image obtained by superimposing a threshold of an exposure dose on a scanogram according to an area of a patient O.

As illustrated in FIG. 4, the image generating unit 60 may superimpose, based on the relationship between the area on the couch top 29 and the threshold Th, a threshold of an exposure dose on the scanogram displayed on the display unit 43 in accordance with the area of the patient O.

The plan acquiring unit 54 acquires information of a scan plan in which at least a relationship between an area on the couch top 29 and an X-ray irradiation time is determined. The scan plan may be modified by a user through the inputting unit 42 as needed.

The plan modification accepting unit 55 accepts an instruction to modify a scan plan from the user through the inputting unit 42.

On receiving an instruction to perform a scan plan from the user through the inputting unit 42, the scan control unit 56 performs the scan by controlling the scanner apparatus 11 via the controller 31 based on the scan plan.

The end determining unit 57 determines whether an instruction to end the examination has been received from the user through the inputting unit 42.

The scan dose estimating unit 58 estimates, before the scan based on the scan plan is performed, the relationship between an area on the couch top 29 and a radiation dose, to be obtained from the scan, and gives the relationship to the image generating unit 60.

The cumulative dose acquiring unit 59 acquires the relationship between the area on the couch top 29 and a historical cumulative radiation dose from the relationship, being stored in the dose history storage unit 48, between the area on the couch top 29 and the radiation dose of each scan, and gives the relationship to the image generating unit 60.

The image generating unit 60 may superimpose, based on the relationship between the area on the couch top 29 and the historical cumulative radiation dose, a cumulative value of an exposure dose of the scanned area on the scanogram in accordance with the area of the patient O (see "scanned area" in FIG. 4). Also, the image generating unit 60 may superimpose an estimated cumulative dose value obtained when the scan to be performed is actually performed, on a scanogram in accordance with the area of the patient O (see "scanned area+ planned area" in FIG. 4) by adding, for each area of couch top 29, the cumulative value of the exposure dose of the scanned area and the dose value being obtained when the scan is performed and having been estimated by the scan dose estimating unit 58.

The historical cumulative radiation dose may be a cumulative dose in the scan performed in the same study as that of the scan to be performed (a cumulative dose in the same study) or may be a cumulative dose in a scan performed previously (e.g., one week before) in another study (a cumulative dose in a past study). Information of a cumulative dose in a past study may be obtained from a medical server not shown via the network connection unit 44.

Next, an exemplary operation of the X-ray CT apparatus 10 according to the present embodiment will be described.

Figure 5:
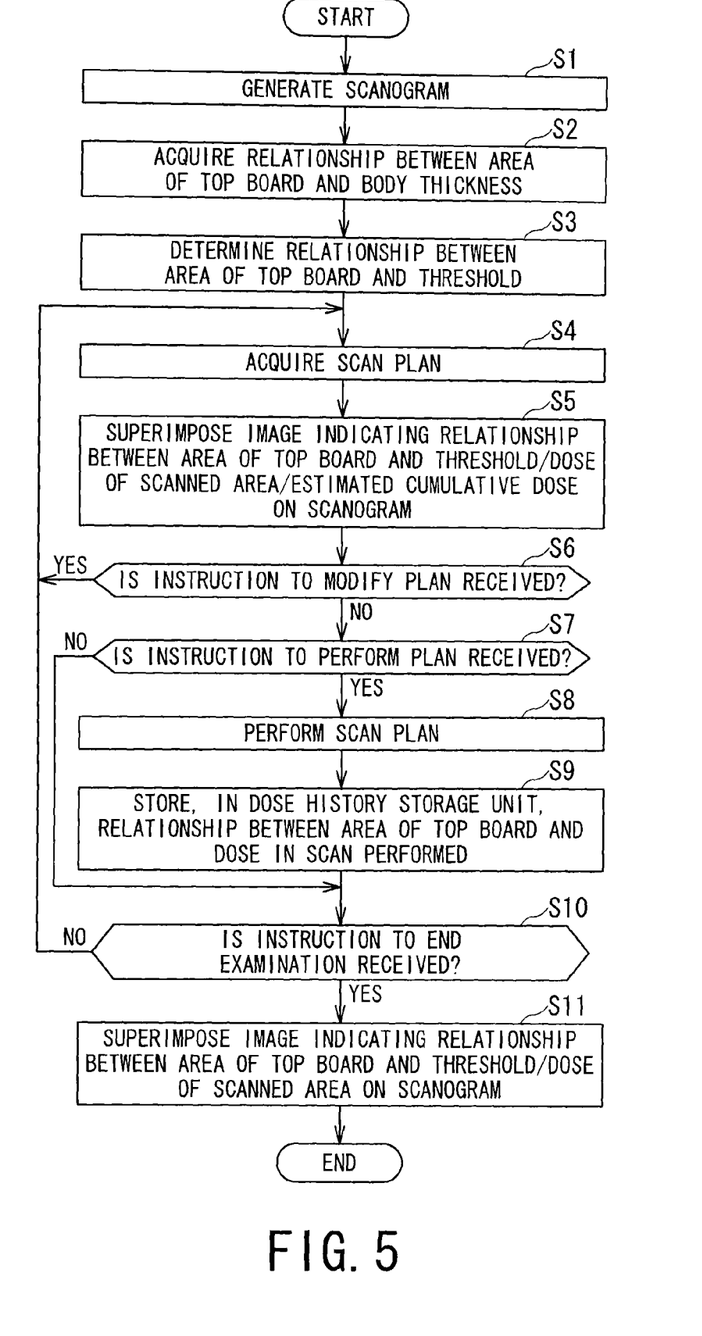
FIG. 5 is a flow chart showing a procedure for presenting, to a user, a threshold of an exposure dose according to the area of the patient by the CPU of the main control unit.

FIG. 5 is a flow chart showing a procedure for presenting, to a user, a threshold of an exposure dose according to the area of the patient O by the CPU of the main control unit 46. In FIG. 5, reference numerals with prefixes S denote steps in the flow chart.

The procedure starts when the body thicknesses and the thresholds of exposure doses are associated with each other and stored in the threshold storage unit 47 in advance.

First, in step S1, the scanogram generating unit 51 generates a scanogram.

Next, in step S2, the body thickness information acquiring unit 52 acquires a relationship between the area of the patient O on the couch top 29 and the body thickness of the patient O based on the scanogram data.

Next, in step S3, the threshold-by-area determining unit 53 searches the threshold storage unit 47 based on the information of the body thickness of the patient O acquired by the body thickness information acquiring unit 52 to obtain the information of an exposure dose threshold Th associated with the body thickness. Then, the threshold-by-area determining unit 53 determines a relationship between the area on the couch top 29 and the threshold Th according to the body thickness of the patient O.

Assume that an age of the patient O is in "adult" of FIG. 2. For example, if the body thickness of the patient O at an area z in a body axis direction on the couch top 29 is 300 mm, the threshold-by-area determining unit 53 determines an exposure dose threshold Th of the patient at the area z on the couch top 29, as Th_C.

Next, in step S4, the plan acquiring unit 54 acquires information of a scan plan in which at least a relationship between areas on the couch top 29 and X-ray irradiation times is determined. If the processing has returned from the step S6, the plan acquiring unit 54 acquires information of a modified scan plan.

Next, in step S5, the image generating unit 60 superimposes on the scanogram an image indicating the relationship between the area on the couch top 29 and the exposure dose threshold Th, determined by the threshold-by-area determining unit 53 (see "threshold" in FIG. 4). Also, the image generating unit 60 obtains, from the cumulative dose acquiring unit 59, the relationship between the area on the couch top 29 and the cumulative dose, and superimposes an image indicating the relationship (see "scanned area" in FIG. 4) on the scanogram.

In addition, the image generating unit 60 superimposes, on the scanogram, an image indicating the relationship between the area on the couch top 29 and an estimated cumulative dose value obtained when the scan based on the scan plan to be performed is actually performed (see "scanned area planned area" in FIG. 4). The user can easily grasp the estimated cumulative dose value obtained when the scan plan is performed, by seeing the image indicating the relationship between the area on the couch top 29, and the estimated cumulative dose value and the threshold, the image being displayed on the display unit 43.

Next, in step S6, the plan modification accepting unit 55 determines whether an instruction to modify the scan plan is received from the user through the inputting unit 42. At this time, the image generating unit 60 may display on the display unit 43 an image that asks the user whether he/she modifies the scan plan. If an instruction to modify the scan plan is received, the processing returns to step S4. On the other hand, if an instruction to modify the scan plan is not received, the processing proceeds to step S7.

Next, in step S7, the scan control unit 56 determines whether an instruction to perform the scan plan is received from the user through the inputting unit 42. At this time, the image generating unit 60 may display on the display unit 43 an image that asks the user whether he/she performs the scan plan. If an instruction to perform the scan plan is received, the processing proceeds to step S8. On the other hand, if an instruction to perform the scan plan is not received, the processing proceeds to step S10.

Next, in step S8, the scan control unit 56 performs the scan by controlling the scanner apparatus 11 via the controller 31 based on the scan plan.

Next, in step S9, the scan control unit 56 stores in the dose history storage unit 48 the relationship between the area on the couch top 29 and a dose in the scan performed in step S8.

Next, in step S10, the end determining unit 57 determines whether an instruction to end the examination is received from the user through the inputting unit 42. If an instruction to end the examination is received, the processing proceeds to step S11. On the other hand, if an instruction to end the examination is not received, the processing returns to step S4 and waits for the input of another scan plan.

Next, in step S11, the image generating unit 60 superimposes on the scanogram an image indicating the relationship between the area on the couch top 29 and the exposure dose threshold Th, determined by the threshold-by-area determining unit 53, and an image indicating the relationship between the area on the couch top 29 and a cumulative dose. Then, the procedure is completed.

With the procedure, a threshold of an exposure dose according to an area of an object can be presented to a user.

The X-ray CT apparatus 10 according to the present embodiment can obtain a threshold of an exposure dose according to a body thickness of each area of the patient O. Thus, according to the X-ray CT apparatus 10, a user can easily grasp, for each area of the patient O, a threshold of an exposure dose, a cumulative dose up to now, and an estimated cumulative dose to be received after a plan is performed. Also, a value according to a body thickness of each area of the patient O may be used as a threshold of an exposure dose.

Therefore, according to the X-ray CT apparatus 10, the user can easily make a plan in which a threshold according to a body thickness of each area of the patient O is taken into consideration, so that it is easy to prevent the patient O from being excessively exposed.

Furthermore, a threshold of an exposure dose may be determined by taking an age into consideration as illustrated in FIG. 2. In addition, according to the X-ray CT apparatus 10 of the present embodiment, the user can easily confirm an irradiation state (cumulative dose) up to now.

Next, the following will describe the case in which if a scan is planned that may lead to an excess over a threshold of an exposure dose depending on an area, the X-ray CT apparatus 10 warns a user that there is an area in which the exposure dose will exceed the threshold or automatically adjusts the dose so as not exceed the threshold.

Figure 6:
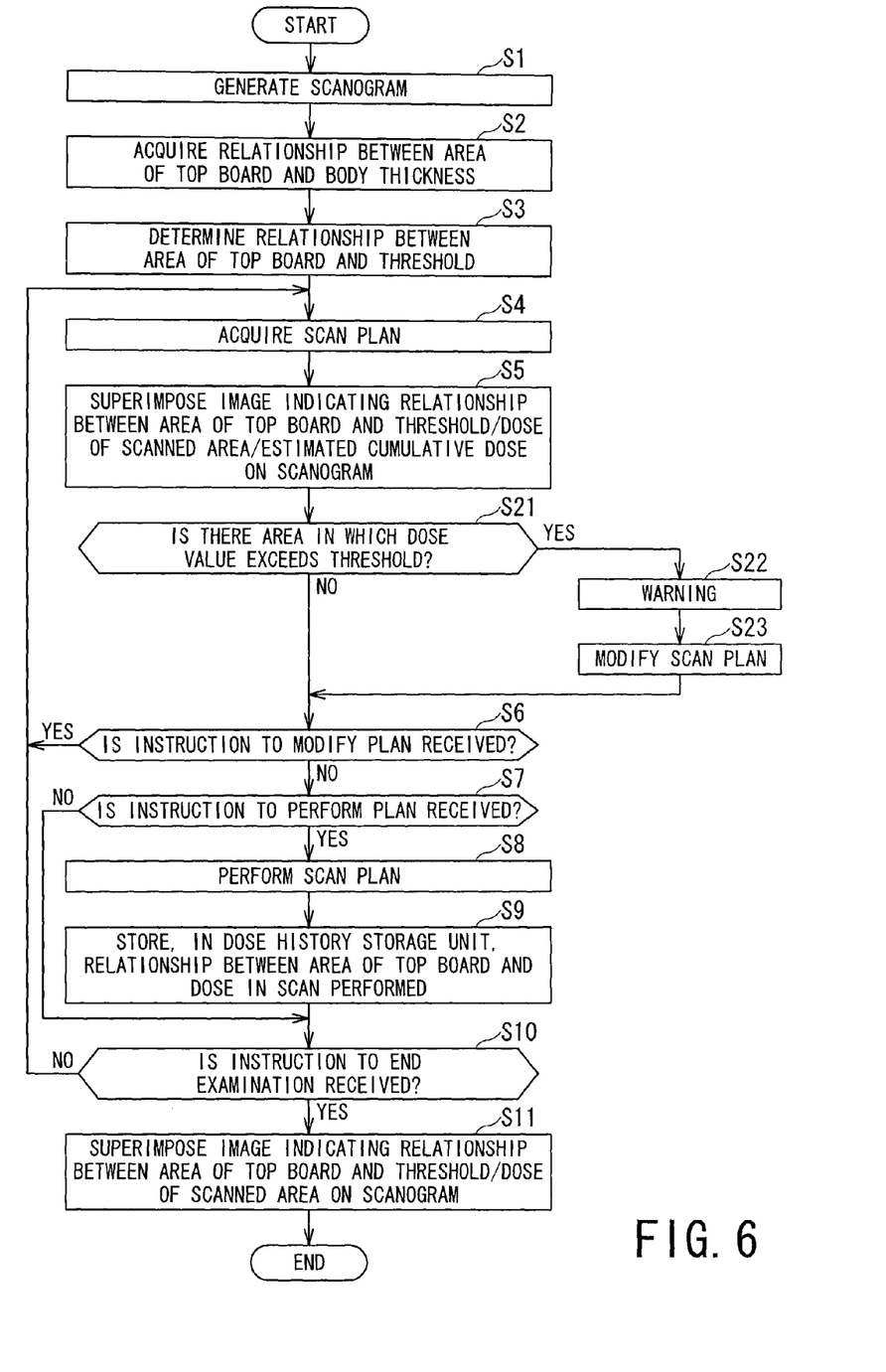
FIG. 6 is a flow chart showing, in addition to the procedure shown in FIG. 5, a procedure for issuing a warning if an exposure dose exceeds a threshold of an exposure dose.

FIG. 6 is a flow chart showing, in addition to the procedure shown in FIG. 5, a procedure for issuing a warning if an exposure dose exceeds a threshold of an exposure dose. The same reference numerals are used for denoting the same steps as those in FIG. 5, and a redundant description thereof is omitted.

If an image as illustrated in FIG. 4 is displayed in step S5, in step S21, the image generating unit 60 compares an estimated cumulative dose value with a threshold and determines whether there is an area on the couch top 29 in which the estimated cumulative dose value may exceed the threshold. For example, the image generating unit 60 determines that an estimated cumulative dose value may exceed a threshold if there is an area on the couch top 29 in which the estimated cumulative dose value is greater than the threshold or there is an area on the couch top 29 in which the estimated cumulative dose value is not greater than the threshold and a difference therebetween is within a predetermined range.

If there is an area on the couch top 29 in which an estimated cumulative dose value may exceed a threshold, the processing proceeds to step S22. On the other hand, if there is no area on the couch top 29 in which an estimated cumulative dose value may exceed a threshold, the processing proceeds to step S6.

In step S22, the image generating unit 60 generates an image for issuing a warning that there is an area on the couch top 29 in which an estimated cumulative dose value may exceed a threshold and superimposes the image on a scanogram. The warning may be issued by using characters, changing the entire color of an image, or changing a displaying manner of the area on the couch top 29 in which an estimated cumulative dose value may exceed a threshold (e.g., changing a color into one different from that of the other area, flashing the area, or the like).

Next, in step S23, the image generating unit 60 modifies the scan plan to adjust a dose so that the estimated cumulative dose value does not exceed the threshold. Examples of dose adjusting methods include a method for modifying a tube current and a tube voltage of the X-ray tube 21, included in a scan plan, and a method for modifying a rotational speed of the rotation unit 25.

If a scan plan is modified, the image generating unit 60 may display information that the scan plan is modified or further superimpose on a scanogram an estimated cumulative dose value received when the modified scan plan is actually performed, in association with an area on the couch top.

Also, the user may set whether a scan plan is automatically modified. For example, if a scan plan is set not to be automatically modified, step S23 is not executed.

Steps S21 to 23 may be executed between steps S5 and S6 as illustrated in FIG. 6, or may be executed between steps S4 and S5, between steps S6 and S7, and between steps S7 and S8. Also, step S23 may not be executed.

For example, if steps S21 to S22 are executed between steps S7 and S8, an instruction to perform the scan plan is received (yes in step S7), and thereafter steps S21 to S22 are executed. At this time, after a warning is issued in step S22, the user may be further asked whether to actually execute the scan plan. Then, if an instruction to perform the plan is received from the user, the processing may proceed to step S8 to perform the scan plan. If an instruction not to perform the plan is received from the user, the processing may return to step S4. Also, if an instruction not to perform the plan is received from the user, a determination of whether to automatically modify the scan plan in step S23 may be further received from the user.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
   a body thickness information acquiring unit configured to acquire information of a body thickness of an object;
   a threshold determining unit configured to determine a threshold of an exposure dose according to the body thickness of the object; and
   an image generating unit configured to generate an image indicating a relationship between the body thickness of the object and the threshold, and superimpose the generated image on an image of the object.

2. The X-ray CT apparatus according to claim 1, further comprising
   a scanogram generating unit configured to generate a scanogram of the object,
   wherein the body thickness information acquiring unit acquires a relationship between an area on a couch top and the body thickness of the object based on a scanogram of the object,
   wherein the threshold determining unit determines the threshold of the exposure dose according to the body thickness of the object and determines a relationship between the area on the couch top and the threshold according to the body thickness of the object, and
   wherein the image generating unit superimposes an image indicating the relationship between the area of the couch top and the threshold on the scanogram and displays the scanogram on a display unit.

3. The X-ray CT apparatus according to claim 2, further comprising:
   a plan acquiring unit configured to acquire information of a scan plan in which at least a relationship between an area on the couch top and an X-ray irradiation time is determined; and
   a scan dose estimating unit configured to, before a scan based on the scan plan is performed, estimate a relationship between an area on the couch top and a radiation dose, the relationship being applied when the scan is performed,
   wherein the image generating unit generates an image indicating the relationship between the area on the couch top and the radiation dose, the relationship being estimated by the scan dose estimating unit, and superimposes, on the scanogram, the image indicating the relationship between the area on the couch top and the radiation dose and the image indicating a relationship between the area of the couch top and the threshold to display the scanogram on the display unit before the scan based on the scan plan is performed.

4. The X-ray CT apparatus according to claim 3, further comprising:
   a dose history storage unit configured to, when a scan is performed, store a relationship between an area on the couch top and a radiation dose in the performed scan; and
   a cumulative dose acquiring unit configured to, from the relationship stored in the dose history storage unit between an area on the couch top and a radiation dose of each scan, acquire a relationship between the area on the couch top and a historical cumulative radiation dose,
   wherein the image generating unit generates an image indicating the relationship between the area on the couch top and the historical cumulative radiation dose and superimposes, on the scanogram, the image indicating the relationship between the area on the couch top and the image indicating the relationship between the area on the couch top and the threshold to display the scanogram on the display unit.

5. The X-ray CT apparatus according to claim 4, wherein
   the plan acquiring unit acquires information of another scan plan after the scan based on the scan plan is performed,
   the scan dose estimating unit estimates, before the scan based on the other scan plan is performed, a relationship between an area on the couch top and a radiation dose, the relationship being obtained when the scan is performed, and determines a cumulative dose obtained by adding the estimated dose and a historical cumulative radiation dose together, thereby estimating a relationship between an area on the couch top and the added cumulative dose, the relationship being obtained when the scan based on the other scan plan is performed, and
   the image generating unit generates a first image indicating the relationship between the area on the couch top and the historical cumulative radiation dose, the relationship being estimated by the scan dose estimating unit and a second image indicating the relationship between the area on the couch top and the added cumulative dose, the relationship being obtained when the scan based on the other scan plan is performed, and superimposes, on the scanogram, the first image, the second image and the image indicating the relationship between the area on the couch top and the threshold to display the scanogram on the display unit before the scan based on the other scan plan is performed.

6. The X-ray CT apparatus according to claim 3, further comprising a plan modification accepting unit configured to accept a modification of the scan plan,
   wherein the scan dose estimating unit estimates, when a modification of the scan plan is accepted, before a scan based on a modified scan plan is performed, a relationship between an area on the couch top and a radiation dose, the relationship being applied when the scan is performed.

7. The X-ray CT apparatus according to claim 3, wherein
   the image generating unit generates, when there is an area on the couch top in which the radiation dose estimated by the scan dose estimating unit is likely to exceed the threshold, an image that issues a warning to that effect and superimposes the image that issues a warning on the scanogram.

8. A method for an X-ray CT apparatus, the method comprising:
   acquiring information of a body thickness of an object;
   determining a threshold of an exposure dose according to the body thickness of the object;
   generating an image indicating a relationship between the body thickness of the object and the threshold; and
   superimposing the generated image on an image of the object.

9. An X-ray CT apparatus comprising:
processing circuitry configured to
- acquire information of a body thickness of an object,
- determine a threshold of an exposure dose according to the body thickness of the object,
- generate an image indicating a relationship between the body thickness of the object and the threshold, and
- superimpose the generated image on an image of the object.

* * * * *